United States Patent

Cotteret et al.

Patent Number: 5,567,421
Date of Patent: Oct. 22, 1996

[54] OXIDATION DYE COMPOSITION FOR KERATINOUS FIBRES COMPRISING A PARA-AMINOPHENOL, A META-AMINOPHENOL AND A PARA-PHENYLENEDIAMINE AND/OR A BIS(PHENYLALKYLENEDIAMINE)

[75] Inventors: Jean Cotteret, Verneuil-sur-Seine; Marie P. Audousset, Levallois-Perret; Alain LaGrange, Coupvray; Jean J. Vandenbosche, Sevran, all of France

[73] Assignee: L'Oreal, Paris, France

[21] Appl. No.: 273,748

[22] Filed: Jul. 13, 1994

[30] Foreign Application Priority Data

Jul. 13, 1993 [FR] France ................... 93 08615

[51] Int. Cl.6 ................................................ A61K 7/13
[52] U.S. Cl. ........................... 424/70.1; 8/408; 8/412
[58] Field of Search ............................ 424/707, 706; 8/408, 412

[56] References Cited

U.S. PATENT DOCUMENTS

| | | | |
|---|---|---|---|
| 4,065,255 | 12/1977 | Andrillion et al. | 8/102 |
| 4,883,656 | 11/1989 | Konrad et al. | 424/70 |

FOREIGN PATENT DOCUMENTS

| | | |
|---|---|---|
| 0182187 | 5/1986 | European Pat. Off. . |
| 0241716 | 10/1987 | European Pat. Off. . |
| 0459901 | 12/1991 | European Pat. Off. . |
| 2315255 | 1/1977 | France . |
| 2421869 | 11/1979 | France . |
| 9300066 | 1/1993 | WIPO . |

*Primary Examiner*—Jyothsna Venkat
*Attorney, Agent, or Firm*—Cushman Darby & Cushman, L.L.P.

[57] ABSTRACT

The invention relates to a dyeing composition for keratinous fibres and in particular for human keratinous fibres such as hair, comprising, in a suitable media for dyeing, at least one oxidation dye precursor chosen from 3-methyl-para-aminophenol, 2-methyl-para-aminophenol and 2-hydroxymethyl-para-aminophenol, and their addition salts with an acid; at least one coupling agent chosen from the 2-methyl-5-aminophenols of formula (I):

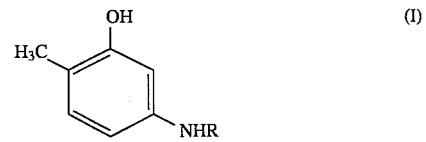

in which R is methyl, ethyl, β-hydroxyethyl or γ-hydroxypropyl, and their addition salts with an acid; and at least one para-phenylenediamine and/or one bis(phenylalkylenediamine) or one of their addition salts with an acid as oxidation dye precursor.

20 Claims, No Drawings

OXIDATION DYE COMPOSITION FOR KERATINOUS FIBRES COMPRISING A PARA-AMINOPHENOL, A META-AMINOPHENOL AND A PARA-PHENYLENEDIAMINE AND/OR A BIS(PHENYLALKYLENEDIAMINE)

The present invention relates to a dyeing composition for keratinous fibres, and in particular for human keratinous fibres, comprising, in combination, at least one para-aminophenol, at least one 2-substituted 5-aminophenol and at least one para-phenylenediamine and/or one bis(phenylalkylenediamine), and to the dyeing process using such a composition and implementing development by an oxidizing agent.

It is known to dye keratinous fibres and in particular human hair, with dyeing compositions containing oxidation dye precursors, in particular ortho- or para-phenylenediamines, ortho- or para-aminophenols, generally known as "oxidation bases" and coupling agents, also known as dyeing modifiers, more particularly aromatic meta-phenylene diamines, meta-aminophenols and meta-diphenols, which allow the "foundation" colourations obtained by the condensation products of the oxidation bases to be modified and to be enriched with glints.

In the field of oxidation dyeing of hair, oxidation dye precursors and coupling agents are sought which allow a colouration having a satisfactory resistance to light, to washing, to bad weather, to perspiration and to the various treatments to which hair may be subjected to be imparted to the hair, and to obtain a wide range of colour shades.

3-Methyl-para-aminophenol, as well as its use in dyeing compositions for keratinous fibres, in combination with 2-methyl-5-aminophenol as coupling agent and paraphenylenediamine or 2,5-diaminotoluene, are known and described in U.S. Pat. No. 4,883,656.

However, such a combination does not provide, after application to keratinous fibres, a sufficiently resistant colouration.

The Applicant has just discovered, and this forms the subject of the invention, that the use of 3-methyl-para-aminophenol, 2-methyl-para-aminophenol and/or 2-hydroxymethyl-para-aminophenol as oxidation dye precursors, in combination with at least one 2-methyl-5-aminophenol of formula (I) defined below as coupling agent, and at least one para-phenylenediamine and/or one bis(phenylalkylenediamine) as oxidation dye precursor, makes it possible to obtain, in the presence of an oxidizing agent, in an acidic or alkaline medium, after application to keratinous fibres and in particular human hair, colourations with red or coppery shades and which have a good resistance to light, to washing, to bad weather, to perspiration and to the various treatments to which hair may be subjected. The resistance to perspiration is particularly noteworthy and superior to that of the prior art.

The subject of the present invention is thus a composition for dyeing keratinous fibres, in particular human keratinous fibres such as hair, comprising, in a suitable medium for dyeing:

- at least one oxidation dye precursor chosen from 3-methyl-para-aminophenol, 2-methyl-para-aminophenol and 2-hydroxymethyl-para-aminophenol, and their addition salts with an acid;
- at least one coupling agent chosen from the 2-methyl-5-aminophenols of formula (I):

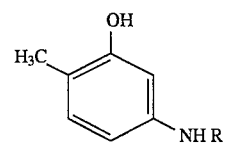

in which R denotes a methyl or ethyl radical or a β-hydroxyethyl or β-hydroxypropyl group; and their addition salts with an acid; and

- at least one oxidation dye precursor chosen from the para-phenylenediamines and the bis(phenylalkylenediamines) of formulae (II) and (III) below, as well as their addition salts with an acid.

The subject of the invention is also a dyeing agent containing several components, the first component of which contains oxidation dye precursors and the coupling agent defined above and the second component an oxidizing agent.

Another subject of the invention relates to the ready-to-use composition, containing the various agents used for dyeing keratinous fibres defined above and an oxidizing agent, in an alkaline or acidic medium.

The invention also concerns a process for dyeing keratinous fibres, and in particular human keratinous fibres such as hair, consisting in applying to these fibres:

- at least one oxidation dye precurser chosen from 3-methyl-para-aminophenol, 2-methyl-para-aminophenol and 2-hydroxymethyl-para-aminophenol and their addition salts with an acid;
- at least one coupling agent chosen from the 2-methyl-5-aminophenols of formula (I) defined above, and their addition salts with an acid;
- at least one para-phenylenediamine of formula (II) defined below and/or at least one bis(phenylalkylenediamine) of formula (III) defined below, or one of their addition salts with an acid, as oxidation dye precursor;

the colour being developed by an oxidizing agent in an acidic or alkaline medium.

According to the invention and among the precursors of para-aminophenol type above, 3-methyl-p-aminophenol is preferred.

Among the coupling agents mentioned above, 2-methyl-5-N-(β-hydroxyethyl)aminophenol is preferred.

The para-phenylenediamines which may be used according to the invention correspond to the formula (II) below:

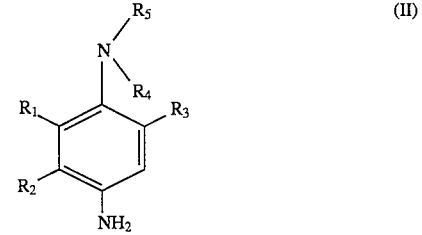

in which:

$R_1$, $R_2$ and $R_3$, which may be identical or different, represent a hydrogen or halogen atom, an alkyl radical, an alkoxy radical, a carboxyl or sulpho radical or a $C_1$–$C_4$ hydroxyalkyl radicals $R_4$ and $R_5$, which may be identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulphoalkyl, piperidinoalkyl or morpholinoalkyl radical or a phenyl radical which is optionally para-substituted with an amino group; or alternatively $R_4$ and $R_5$ form, together with the nitrogen atom to which they are attached, a piperidino or morpholino heterocycle, with the proviso that $R_1$ or $R_3$ represents a hydrogen atom when $R_4$ and $R_5$ do not represent a hydrogen atom. These alkyl or alkoxy radicals preferably have 1 to 4 carbon atoms and in particular denote methyl, ethyl, propyl, methoxy and ethoxy radicals.

Among the compounds of formula (II), there may more particularly be mentioned para-phenylenediamine, para-toluylenediamine, methoxy-para-phenylenediamine, chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 3-methyl- 4-amino-N,N-diethylaniline, N,N-di(β-hydroxyethyl)paraphenylenediamine, 3-methyl-4-amino-N,N-di(β-hydroxyethyl)aniline, 3- chloro-4-amino-N, N-di(β-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-aetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine, N-(4-aminophenyl)piperidine, 2-(β-hydroxyethyl)para-phenylenediamine, fluoro-para -phenylenediamine, carboxy-para-phenylenediamine, sulpho-para-phenylenediamine, 2-isopropyl-para-phenylenediamine, 2-n-propyl-paraphenylenediamine, N-(β-hydroxypropyl) -para-phenylenediamine, 2-hydroxymethyl-para-phenylenediamine, N,N-dimethyl- 3-methyl-para-phenylenediamine, N-ethyl-N-(β-hydroxyethyl)para-phenylenediamine, N-(dihydroxypropyl)-para-phenylenediamine, N-(4-aminophenyl)para-phenylenediamine and N-phenyl-para-phenylenediamine.

These para-phenylenediamines may be used either in free base form or in salt form, such as the hydrochloride, hydrobromide or sulphate salt form.

Among the compounds of formula (II), the following are preferred:

para-phenylenediamine, para-toluylenediamine, 2,6-dimethyl-para-phenylenediamine, 2- hydroxymethyl-para-phenylenediamine, 2-(β-hydroxyethyl)para-phenylenediamine, 2-n-propyl-para-phenylenediamine, 2-isopropyl-para-phenylenediamine, N-(β- hydroxypropyl)para-phenylenediamine, N,N-di(β-hydroxyethyl)para-phenylenediamine, 4-amino-N-(β-methoxyethyl)aniline, and their salts.

The so-called double bases are the bis(phenylalkylenediamines), corresponding to the formula:

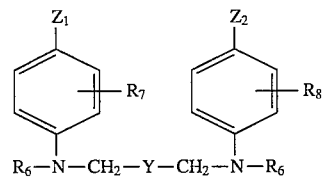

(III)

in which:

$Z_1$ and $Z_2$, which may be identical or different, represent hydroxyl groups or groups $NHR_9$, where $R_9$ denotes a hydrogen atom or a lower alkyl radical;

$R_7$ and $R_8$, which may be identical or different, represent either hydrogen atoms or halogen atoms or alternatively alkyl groups;

$R_6$ represents a hydrogen atom or an alkyl, hydroxyalkyl or aminoalkyl group in which the amino residue may be substituted;

Y represents a radical taken from the group consisting of the following radicals:

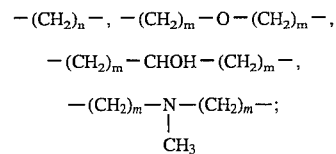

n being an integer between 0 and 8 and m an integer between 0 and 4, it being also possible for these bases to take the form of their addition salts with acids.

The alkyl or alkoxy radicals mentioned above preferably denote a group having 1 to 4 carbon atoms and in particular methyl, ethyl, propyl, methoxy and ethoxy.

Among the compounds of formula (III) there may be mentioned N,N'-bis(β-hydroxyethyl)-N,N'-bis(4-aminophenyl)- 1,3-diamino-2-propanol, N,N'-bis-(β-hydroxyethyl)-N,N'-bis( 4-aminophenyl)ethylenediamine, N, N-bis (4-aminophenyl)tetramethylenediamine, N,N'-bis(β-hydroxyethyl)-N,N'-bis( 4-aminophenyl) tetramethylenediamine, N,N'-bis (4-methylaminophenyl) tetramethylenediamine, N,N'-bis(ethyl)-N,N'-bis( 4'-amino-3'-methylphenyl)ethylenediamine, and their salts.

N,N'-bis(β-Hydroxyethyl)-N,N'-bis(4'-aminophenyl)- 1,3- diamino-2-propanol is particularly preferred.

According to the process in accordance with the invention, at least one composition (A) is applied to human keratinous fibres, containing, in a suitable medium for dyeing:

at least one oxidation dye precursor chosen from 3-methyl-para-aminophenol, 2-methyl-para-amino phenol, 2-hydroxymethyl-para-aminophenol, and their salts;

at least one coupling agent chosen from the 2-methyl-5-aminophenols of formula (I) defined above, and their salts;

at least one para-phenylenediamine of formula (II) and/or one bis(phenylalkylenediamine) of formula (III) or their salts, as oxidation dye precursors, the colour being developed in an acidic or alkaline medium, using an oxidizing agent which is added just at the moment of use to the composition (A) or which is present in a composition (B) which is applied simultaneously or sequentially in a separate manner.

The subject of the invention is also dyeing devices or "kits" containing several compartments, allowing the process indicated above to be implemented.

Such a dyeing kit contains at least two compartments, the first of which contains the composition (A) as defined above and the second contains the composition (B) comprising an oxidizing agent in a suitable medium for dyeing.

Other subjects of the invention will become apparent on reading the description and the examples which follow.

The acid salts used according to the invention are preferably chosen from hydrochlorides, sulphates, hydrobromides and tartrates.

3-Methyl-para-aminophenol, 2-methyl-para-aminophenol and 2-hydroxymethyl-para-aminophenol or their salts are present at a total concentration of 0.01% to 4% by weight relative to the total weight of the dyeing composition, and preferably from 0.1 to 2% by weight.

The 2-methyl-5-aminophenols of formula (I) and their salts represent in total from 0.005% to 5% by weight relative to the total weight of the dyeing composition, and preferably from 0.01 to 3.5% by weight.

The para-phenylenediamines and/or the bis(phenylalkylenediamines) represent from 0.01% to 8% by weight relative to the total weight of the dyeing composition, and preferably from 0.1 to 4% by weight.

The set of oxidation dye precursors and coupling agents according to the invention represents from 0.1 to 10% by weight, and preferably from 0.4 to 7% by weight, relative to the total weight of the composition.

The oxidizing agent is preferably chosen from hydrogen peroxide, urea peroxide, alkali metal bromates and persalts such as perborates and persulphates. Hydrogen peroxide is particularly preferred.

The composition (A), which contains the combination of dyes as described above, may have a pH between 3 and 10.5, which may be adjusted to the chosen value using basifying agents commonly used in the dyeing of keratinous fibres, such as aqueous ammonia, alkali metal carbonates, alkanolamines, for example mono-, di- and triethanolamines and their derivatives, sodium or potassium hydroxides, the compounds of formula:

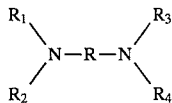

in which:

R is a propylene residue which is optionally substituted with a hydroxyl group or with a $C_1-C_4$ alkyl radical;

$R_1$, $R_2$, $R_3$ and $R_4$, simultaneously or independently of each other, represent a hydrogen atom, a $C_1-C_4$ alkyl radical or a $C_1-C_4$ hydroxyalkyl radical; or standard acidifying agents, such as inorganic or organic acids, for example hydrochloric, tartaric, citric and phosphoric acids.

The pH of the composition (B) containing the oxidizing agent as defined above is such that after mixing with the composition (A), the pH of the composition applied to human keratinous fibres preferably varies between 3 and 11. It is adjusted to the desired value using acidifying or possibly basifying agents which are well known in the state of the art, as described above.

The oxidizing composition (B) preferably consists of hydrogen peroxide solution.

According to a preferred embodiment of the dyeing process of the invention, the dyeing composition (A) described above is mixed at the moment of use with an oxidizing solution in a sufficient amount to develop a colouration. The mixture obtained is subsequently applied to human keratinous fibres and is left to stand for 5 to 40 minutes, preferably 15 to 30 minutes, after which the fibres are rinsed, washed with shampoo, rinsed again and dried.

According to the invention, the dyeing compositions may contain, in addition to the dyes defined above, other coupling agents and/or direct dyes, in particular for the purpose of tinting or enriching with glints the colourations provided by the oxidation dye precursors.

These coupling agents are well known per se and are chosen from benzene compounds bearing at least 2 hydroxyl and/or optionally modified amino substitutions in a meta position with respect to each other and which are different from 2-methyl-5-aminophenol and the 2-methyl-5-aminophenols of formula (I); α-naphthol; indole derivatives; coupling agents possessing an active methylene group, such as β-keto compounds; pyrazolones; as well as their salts.

The direct dyes are preferably azo or anthraquinone dyes or nitro derivatives of the benzene series.

The dyeing compositions in accordance with the invention also contain, in their preferred embodiment, anionic, cationic, nonionic or amphoteric surface-active agents or their mixtures. Among these surface-active agents there may be mentioned alkylbenzene sulphonates, alkylnaphthalene sulphonates, sulphates, ether sulphates and fatty alcohol sulphonates, alkylpolyglycosides, quaternary ammonium salts such as trimethylcetylammonium bromide, cetylpyridinium bromide, optionally oxyethylenated fatty acid ethanolamides, polyoxyethyenated acids, alcohols and a mines, polyglycerolated fatty alcohols, and polyoxyethylenated or polyglycerolated alkylphenols, as well as polyoxyethylenated alkyl sulphates.

These surface-active agents are present in the compositions in accordance with the invention in proportions between 0.5 and 55% by weight and preferably between 2 and 50% by weight relative to the total weight of the composition.

These compositions may also contain organic solvents for dissolving the compounds which would not be sufficiently soluble in water. Among these solvents, there may be mentioned, by way of example, $C_1-C_4$ lower alkanols such as ethanol and isopropanol; glycerol, glycols or glycol ethers such as 2-butoxyethanol, propylene glycol, the monoethyl ether and the monomethyl ether of diethylene glycol, and aromatic alcohols such as benzyl alcohol or phenoxyethanol, analogous products and their mixtures.

The solvents are preferably present in proportions between 1 and 40% by weight and in particular between 5 and 30% by weight relative to the total weight of the composition.

The thickening agents which may be added to the compositions in accordance with the invention may be chosen from sodium alginate, gum arabic, optionally crosslinked acrylic acid polymers, cellulose derivatives and heterobiopolysaccharides such as xanthan gum, and inorganic thickening agents such as bentonite may also be used.

These thickening agents are preferably present in proportions between 0.1 and 5% and in particular between 0.2 and 3% by weight relative to the total weight of the composition.

The antioxidants which may be present in the compositions are chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid.

These antioxidants are present in the composition in proportions between 0.05 and 1.5% by weight relative to the total weight of the composition.

These compositions may also contain other cosmetically acceptable adjuvants, such as for example penetration agents, sequestrating agents, perfumes, buffers, dispersing agents, treatment agents, conditioning agents, film-forming agents, preservatives and opacifying agents.

The composition applied to hair may be provided in various forms, such as in liquid, cream or gel form or any other form which is suitable for dyeing keratinous fibres and in particular human hair. These compositions may be packaged under pressure in aerosol cans in the presence of a propellent and may form foams.

The examples which follow are intended to illustrate the invention without, however, presenting a limiting nature.

EXAMPLE 1

The following dyeing composition is prepared:
Polyglycerolated oleyl alcohol containing 2 mol of glycerol 5.0 g
Polyglycerolated oleyl alcohol containing 4 mol of glycerol 5.0 g
Oleic acid 5.0 g
Oleic diethanolamine 5.0 g
Oleic diethanolamide 12.0 g
Ethyl alcohol 10.0 g
2-Ethoxyethanol 12.0 g
Ethylenediaminetetraacetic acid 0.2 g
2-Methyl-5-N-(β-hydroxyethyl)aminophenol 1.0 g
3-Methyl-p-aminophenol 0.8 g
p-phenylenediamine 0.4 g
Aqueous sodium metabisulphite solution containing 35% of AM 1.3 g
2-Methylhydroquinone 0.17 g
Aqueous ammonia containing 20% of NH$_3$ 10.2 g
Water qs 100 g At the time of use, this composition is mixed, weight for weight, with 20 volumes hydrogen peroxide (6% by weight) the pH of which is 3.

The pH of the mixture is 10.

This mixture is applied to natural grey hair containing 90% white hair for 30 minutes.

After rinsing, the hair is shampooed, rinsed again and dried. The hair is dyed a medium iridescent coppery colour.

EXAMPLE 2

The procedure is performed in the same manner as in Example 1, except that the dyeing composition contains 1.36 g of 2-methyl-5-N-(β-hydroxyethyl)aminophenol.

The colour obtained on grey hair containing 90% permanent-waved white hair is a deep coppery red.

EXAMPLE 3

The procedure is performed in the same way as in Example 1, except that the dyeing composition contains as colouring agents:
2-Methyl-5-N-(β-hydroxyethyl)aminophenol 1.2 g
3-Methyl-p-aminophenol 0.6 g
Para-toluylenediamine.2 HCl 0.6 g The colour obtained on natural grey hair containing 90% white hair is a slightly iridescent medium coppery colour.

EXAMPLE 4

The procedure is performed as in Example 3, except that the dyeing composition contains 1.63 g of 2-methyl- 5-N-(β-hydroxyethyl)aminophenol.

The colour obtained on grey hair containing 90% permanent-waved white hair is a deep iridescent red.

EXAMPLES 5 to 7

The following dyeing composition is prepared:
Polyglycerolated oleyl alcohol containing 2 mol of glycerol 4.0 g
Polyglycerolated oleyl alcohol containing 4 mol of glycerol (78% of AM) 5.7 g AM
Oleic acid 3.0 g
Oxyethylenated oleic amine containing 2 mol of ethylene oxide, sold under the name ETHOMEEN 012 by the company AKZO 7.0 g
Diethylaminopropyl laurylaminosuccinamate, sodium salt containing 55% of AM 3.0 g AM
Oleyl alcohol 5.0 g
Oleic acid diethanolamide 12.0 g
Propylene glycol 3.5 g 3.5 g
Ethyl alcohol 7.0 g
Dipropylene glycol 0.5 g
Propylene glycol monomethyl ether 9.0 g
Aqueous sodium metabisulphite solution containing 35% of AM 0.46 g AM
Ammonium acetate 0.8 g
Antioxidant, sequestrating agent qs
Perfume, preservative qs
Aqueous ammonia containing 20% of NH$_3$ 10.0 g
Colouring agents x g
Demineralized water qs 100 g At the time of use, this composition is mixed, weight for weight, with hydrogen peroxide titrating at 20 volumes (6% by weight), of pH 3.

A mixture is obtained of pH indicated in the table below.

This mixture is applied to grey hair containing 90% natural or permanent-waved white hair for 30 minutes. After rinsing, washing with shampoo, rinsing and drying, the hair is dyed in the shades indicated in the table below.

TABLE

| Example | 5 | 6 | 7 |
|---|---|---|---|
| 3-methyl-p-aminophenol | 0.2 g | 0.4 g | |
| 2-methyl-p-aminophenol | | | 0.5 g |
| 2-hydroxymethyl-p-amino-phenol | | | 0.5 g |
| 2-methyl-5-N-(β-hydroxy-ethyl)amino-phenol | 0.5 g | 0.8 g | 0.5 g |
| 2-n-propyl-p-phenylene-diamine p-phenylenediamine | | 0.01 g | |
| 2-β-hydroxyethyl dihydro-chloride p-phenylenediamine | 0.01 g | | 0.1 g |
| 2,6-dimethyl dihydrochloride p-phenylenediamine | 0.01 g | | |
| 2-isopropyl dihydrochloride p-phenylenediamine | 0.01 g | | |
| 4-amino dihydrochloride N-(β-methoxyethyl)aniline | | 0.02 g | |
| pH of the mixture | 9.7 | 9.6 | 9.8 |
| SHADE OBTAINED: | | | |
| * on natural grey hair containing 90% white hair | | Iridescent coppery | |
| * on permanent-waved grey hair containing 90% white hair | Slightly iridescent coppery | | Coppery golden |

We claim:

1. A composition for dyeing keratinous fibers comprising in a medium suitable for dyeing said keratinous fibers,
    (a) at least one oxidation dye precursor selected from the group consisting of 3-methyl-para-aminophenol, 2-methyl-para-aminophenol, 2-hydroxymethyl-para-aminophenol and an acid addition salt thereof;

(b) at least one coupling agent selected from the group consisting of a 2-methyl-5-aminophenol of formula (I) and an acid addition salt thereof

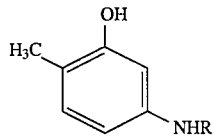 (I)

wherein

R represents methyl, ethyl, β-hydroxyethyl or γ-hydroxypropyl; and (c) at least one oxidation dye precursor selected from the group consisting of (i) a para-phenylenediamine of formula (II)

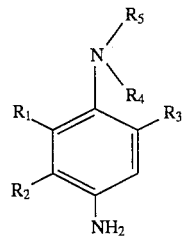 (II)

wherein $R_1$, $R_2$ and $R_3$, each independently, represent hydrogen, halogen, $C_1$–$C_4$ alkyl, $C_1$–$C_4$ alkoxy, a carboxyl radical, a sulpho radical or $C_1$–$C_4$ hydroxyalkyl, $R_4$ and $R_5$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, sulphoalkyl, piperidinoalkyl, morpholinoalkyl, the alkyl groups being in each occurrence $C_1$–$C_4$ alkyl groups or phenyl optionally para-substituted with an amino group, or $R_4$ and $R_5$ together with the nitrogen atom to which $R_4$ and $R_5$ are attached form a piperidino or morpholino heterocycle, with the proviso that $R_1$ or $R_3$ represent a hydrogen when $R_4$ and $R_5$ do not represent hydrogen;

(ii) a bis(phenylalkylenediamine) of formula (III)

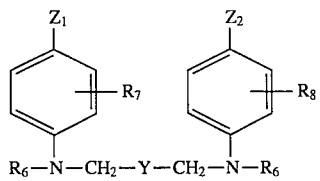 (III)

wherein $Z_1$ and $Z_2$, each independently, represent hydroxyl or $NHR_9$ wherein $R_9$ represents hydrogen or lower $C_1$–$C_4$ alkyl;

$R_7$ and $R_8$, each independently, represent hydrogen, halogen or $C_1$–$C_4$ alkyl;

$R_6$ represents hydrogen, $C_1$–$C_4$ alkyl, $C_1$–$C_4$ hydroxyalkyl or amino $C_1$–$C_4$ alkyl;

Y represents a member selected from the group consisting of —$(CH_2)_n$—, —$(CH_2)_m$—O—$(CH_2)_m$—, —$(CH_2)_m$—CHOH—$(CH_2)_m$— and

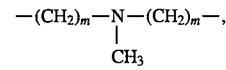

wherein n is an integer ranging from 0 to 8 and m is an integer ranging from 0 to 4; and an acid addition salt of (i) or (ii).

2. The composition of claim 1 wherein said oxidation dye precursor (a) is 3-methyl-para-aminophenol or an acid addition salt thereof.

3. The composition of claim 1 wherein said coupling agent is 2-methyl-5-N-(β-hydroxyethyl) aminophenol or an acid addition salt thereof.

4. The composition of claim 1 wherein said paraphenylenediamine of formula (II) is selected from the group of
paraphenylenediamine,
paratoluylenediamine,
2,6-dimethyl-paraphenylenediamine,
2-hydroxymethyl-paraphenylenediamine,
2-(β-hydroxyethyl)paraphenylenediamine,
2-n-propyl-paraphenylenediamine,
2-isopropyl-paraphenylenediamine,
N-(β-hydroxypropyl)paraphenylenediamine,
N,N-di(β-hydroxyethyl)paraphenylenediamine,
4-amino-N-(β-methoxyethyl)aniline, and
an acid addition salt thereof.

5. The composition of claim 1 wherein said bis(phenylalkylenediamine) of formula (III) is N,N'-bis(β-hydroxyethyl)-N,N'-bis(4-aminophenyl)-1,3-diamino-2-propanol or an acid addition salt thereof.

6. The composition of claim 1 wherein said acid addition salt is a hydrochloride, a sulphate, a hydrobromide or a tartrate.

7. The composition of claim 1 wherein said oxidation dye precursor (a) or the acid addition salt thereof is present in an amount ranging from 0.01 to 4 percent by weight based on the total weight of said composition.

8. The composition of claim 1 wherein said oxidation dye precursor (a) or the acid addition salt thereof is present in an amount ranging from 0.1 to 2 percent by weight based on the total weight of said composition.

9. The composition of claim 1 wherein said 2-methyl-5-aminophenol of formula (I) or an acid addition salt thereof is present in an amount ranging from 0.005 to 5 percent by weight based on the total weight of said composition.

10. The composition of claim 1 wherein said 2-methyl-5-aminophenol of formula (I) or an acid addition salt thereof is present in an amount ranging from 0.01 to 3.5 percent by weight based on the total weight of said composition.

11. The composition of claim 1 wherein said oxidation dye precursor (c) is present in an amount ranging from 0.01 to 8 percent by weight based on the total weight of said composition.

12. The composition of claim 1 wherein said oxidation dye precursor (c) is present in an amount ranging from 0.01 to 4 percent by weight based on the total weight of said composition.

13. The composition of claim 1 wherein the combined total concentration of said oxidation dye precursors and said coupling agent ranges from 0.1 to 10 percent by weight based on the total weight of said composition.

14. The composition of claim 1 wherein the combined total concentration of said oxidation dye precursors and said coupling agent ranges from 0.4 to 7 percent by weight based on the total weight of said composition.

15. The composition of claim 1 wherein the pH ranges from 3 to 10.5.

16. The composition of claim 1 additionally containing a direct dye selected from the group consisting of an azo dye, an anthraquinone dye and a nitrobenzene dye.

17. The composition of claim 1 additionally containing at least one adjuvant selected from the group consisting of (i) an anionic, cationic, nonionic or an amphoteric surface-active agent or a mixture thereof present in an amount ranging from 0.5 to 55 percent by weight based on the total weight of said composition;

(ii) an organic solvent present in an amount ranging from 1 to 40 percent by weight based on the total weight of said composition;

(iii) a thickening agent present in an amount ranging from 0.1 to 5 percent by weight based on the total weight of said composition; and (iv) an antioxidant present in an amount ranging from 0.05 to 1.5 percent by weight based on the total weight of said composition.

18. The composition of claim 1 also containing an additive selected from the group consisting of a penetration agent, a sequestering agent, a perfume, a buffer, a dispersing agent, a conditioning agent, a film-forming agent, a preservative and an opacifying agent.

19. A dyeing agent for keratinous fibers comprising, in a medium suitable for dyeing said, keratinous fibers, a combination of (a) a component (A) comprising said composition of claim 1; and (b) a component (B) comprising an oxidizing agent.

20. The dyeing agent of claim 19 wherein said oxidizing agent is selected from the group consisting of hydrogen peroxide, urea peroxide, an alkali metal bromate, a perborate and a persulphate.

* * * * *